US009282907B2

(12) United States Patent
Ghosh

(10) Patent No.: US 9,282,907 B2
(45) Date of Patent: Mar. 15, 2016

(54) IDENTIFICATION OF HEALTHY VERSUS UNHEALTHY SUBSTRATE FOR PACING FROM A MULTIPOLAR LEAD

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/948,568

(22) Filed: Jul. 23, 2013

(65) Prior Publication Data
US 2015/0032016 A1    Jan. 29, 2015

(51) Int. Cl.
| A61B 5/04 | (2006.01) |
| A61B 5/00 | (2006.01) |
| A61B 5/044 | (2006.01) |
| A61B 5/0408 | (2006.01) |
| A61B 5/0472 | (2006.01) |
| A61B 5/0468 | (2006.01) |
| A61B 5/0402 | (2006.01) |
| A61B 5/0452 | (2006.01) |

(52) U.S. Cl.
CPC .......... *A61B 5/04012* (2013.01); *A61B 5/0402* (2013.01); *A61B 5/044* (2013.01); *A61B 5/0408* (2013.01); *A61B 5/0452* (2013.01); *A61B 5/0468* (2013.01); *A61B 5/0472* (2013.01); *A61B 5/6823* (2013.01)

(58) Field of Classification Search
CPC .......... A61B 5/02028; A61B 5/04011; A61B 5/04068; A61B 5/0472
USPC ................................. 600/508–509
See application file for complete search history.

(56) References Cited

U.S. PATENT DOCUMENTS

| 4,233,987 A | 11/1980 | Feingold |
| 4,428,378 A | 1/1984 | Anderson et al. |
| 4,497,326 A | 2/1985 | Curry |
| 4,566,456 A | 1/1986 | Koning et al. |
| 4,674,511 A | 6/1987 | Cartmell |
| 5,052,388 A | 10/1991 | Sivula et al. |
| 5,054,496 A | 10/1991 | Wen |

(Continued)

FOREIGN PATENT DOCUMENTS

| EP | 1 072 284 A2 | 1/2001 |
| EP | 1 504 713 A1 | 2/2005 |

(Continued)

OTHER PUBLICATIONS

Dawoud, F. et al., "Inverse Electrocardiographic Imaging to Assess Electrical Dyssynchorny in Cardiac Resynchronization Therapy Patients" Computing in Cardiology, 2012; 39:993-996.

(Continued)

Primary Examiner — Paula J Stice
(74) Attorney, Agent, or Firm — Carol F. Barry

(57) ABSTRACT

A medical device system performs a method determining presence of scar tissue. Torso-surface potential signals are received by a processor from multiple electrodes distributed on a torso of a patient. The processor extracts features of the potential signal from each electrode and stores values of the features in a non-transitory storage medium. The processor determines a scar indicator index for each of the electrodes from the stored features and identifies which ones of the electrodes have an affirmative scar indicator index. An overall scar burden index is determined as a proportion of the electrodes with an affirmative scar indicator index.

22 Claims, 7 Drawing Sheets

(56) References Cited

U.S. PATENT DOCUMENTS

| | | |
|---|---|---|
| 5,311,873 A | 5/1994 | Savard |
| 5,443,492 A | 8/1995 | Stokes et al. |
| 5,628,778 A | 5/1997 | Kruse et al. |
| 5,671,752 A | 9/1997 | Sinderby et al. |
| 5,683,432 A | 11/1997 | Goedeke et al. |
| 5,810,740 A | 9/1998 | Paisner |
| 5,891,045 A | 4/1999 | Albrecht et al. |
| 5,922,014 A | 7/1999 | Warman et al. |
| 6,055,448 A | 4/2000 | Anderson et al. |
| 6,187,032 B1 | 2/2001 | Ohyu et al. |
| 6,236,883 B1 | 5/2001 | Ciaccio et al. |
| 6,311,089 B1 | 10/2001 | Mann et al. |
| 6,381,493 B1 | 4/2002 | Stadler et al. |
| 6,393,316 B1 | 5/2002 | Gillberg et al. |
| 6,418,346 B1 | 7/2002 | Nelson |
| 6,442,433 B1 | 8/2002 | Linberg |
| 6,473,638 B2 | 10/2002 | Ferek-Petric |
| 6,480,745 B2 | 11/2002 | Nelson |
| 6,507,756 B1 | 1/2003 | Heynen et al. |
| 6,584,343 B1 | 6/2003 | Ransbury et al. |
| 6,599,250 B2 | 7/2003 | Webb |
| 6,640,136 B1 | 10/2003 | Helland et al. |
| 6,772,004 B2 | 8/2004 | Rudy |
| 6,804,555 B2 | 10/2004 | Warkentin |
| 6,856,830 B2 | 2/2005 | He |
| 6,882,882 B2 | 4/2005 | Struble et al. |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,031,777 B2 | 4/2006 | Hine et al. |
| 7,092,759 B2 | 8/2006 | Nehls et al. |
| 7,142,922 B2 | 11/2006 | Spinelli et al. |
| 7,184,835 B2 | 2/2007 | Kramer et al. |
| 7,215,998 B2 | 5/2007 | Wesselink et al. |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz |
| 7,953,475 B2 | 5/2011 | Harlev et al. |
| 7,953,482 B2 | 5/2011 | Hess |
| 7,983,743 B2 | 7/2011 | Rudy et al. |
| 7,996,063 B2 | 8/2011 | Vass et al. |
| 8,010,194 B2 | 8/2011 | Muller |
| 8,019,409 B2 | 9/2011 | Rosenberg et al. |
| 8,032,229 B2 | 10/2011 | Gerber et al. |
| 8,036,743 B2 | 10/2011 | Savage |
| 8,060,185 B2 | 11/2011 | Hunter et al. |
| 8,150,513 B2 | 4/2012 | Chinchoy |
| 8,160,700 B1 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,527,051 B1 | 9/2013 | Hedberg et al. |
| 8,583,230 B2 | 11/2013 | Ryu et al. |
| 8,617,082 B2 | 12/2013 | Zhang et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,805,504 B2 | 8/2014 | Sweeney |
| 2002/0161307 A1 | 10/2002 | Yu et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0122479 A1 | 6/2004 | Spinelli et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0096522 A1 | 5/2005 | Reddy et al. |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0253162 A1 | 11/2006 | Zhang et al. |
| 2007/0142871 A1 | 6/2007 | Libbus et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam |
| 2009/0099619 A1 | 4/2009 | Lessmeier et al. |
| 2009/0112109 A1 | 4/2009 | Kuklik |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |

(56) References Cited

U.S. PATENT DOCUMENTS

| | | |
|---|---|---|
| 2010/0022873 A1 | 1/2010 | Hunter et al. |
| 2010/0049063 A1 | 2/2010 | Dobak, III |
| 2010/0069987 A1 | 3/2010 | Min |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0174137 A1 | 7/2010 | Shim |
| 2010/0198292 A1 | 8/2010 | Honeck et al. |
| 2010/0228138 A1 | 9/2010 | Chen |
| 2010/0268059 A1 | 10/2010 | Ryu et al. |
| 2011/0004111 A1 | 1/2011 | Gill |
| 2011/0004264 A1 | 1/2011 | Siejko et al. |
| 2011/0022112 A1 | 1/2011 | Min |
| 2011/0054286 A1 | 3/2011 | Crosby |
| 2011/0054560 A1 | 3/2011 | Rosenberg et al. |
| 2011/0092809 A1 | 4/2011 | Nguyen et al. |
| 2011/0112398 A1 | 5/2011 | Zarkh et al. |
| 2011/0118803 A1 | 5/2011 | Hou |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0283587 A1 | 11/2012 | Ghosh |
| 2012/0284003 A1 | 11/2012 | Ghosh |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0304407 A1 | 11/2013 | George et al. |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032172 A1 | 1/2015 | Ghosh |
| 2015/0032173 A1 | 1/2015 | Ghosh |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0265840 A1 | 9/2015 | Ghosh et al. |

FOREIGN PATENT DOCUMENTS

| | | |
|---|---|---|
| EP | 2016976 A1 | 1/2009 |
| EP | 2391270 A1 | 7/2011 |
| EP | 1 925 337 B1 | 3/2012 |
| EP | 2436309 A2 | 4/2012 |
| EP | 2 435 132 B1 | 8/2013 |
| WO | 98/26712 A1 | 6/1998 |
| WO | 00/45700 A1 | 8/2000 |
| WO | 01/67950 A1 | 9/2001 |
| WO | 2005/056108 A2 | 6/2005 |
| WO | 2006/105474 A2 | 10/2006 |
| WO | 2006/115777 A1 | 11/2006 |
| WO | 2006/117773 A1 | 11/2006 |
| WO | 2007/013994 A2 | 2/2007 |
| WO | 2007/013994 A3 | 4/2007 |
| WO | 2007/139456 A1 | 12/2007 |
| WO | 2008/151077 A2 | 12/2008 |
| WO | 2009/079344 A1 | 6/2009 |
| WO | 2009/139911 A2 | 11/2009 |
| WO | 2009/148429 A1 | 12/2009 |
| WO | 2010/019494 A1 | 2/2010 |
| WO | 2010/071520 A1 | 6/2010 |
| WO | 2010/088040 A1 | 8/2010 |
| WO | 2010/088485 A1 | 8/2010 |
| WO | 2011/070166 A1 | 6/2011 |
| WO | 2011/090622 A1 | 7/2011 |
| WO | 2011/099992 A1 | 8/2011 |
| WO | 2012/037471 A2 | 3/2012 |
| WO | 2012/037471 A3 | 6/2012 |
| WO | 2012/106297 A2 | 8/2012 |
| WO | 2012/106297 A3 | 8/2012 |
| WO | 2012/109618 A2 | 8/2012 |
| WO | 2012/110940 A1 | 8/2012 |
| WO | 2012/109618 A3 | 11/2012 |
| WO | 2012/151364 A1 | 11/2012 |
| WO | 2012/151389 A1 | 11/2012 |
| WO | 2013/006724 A2 | 1/2013 |
| WO | 2013/010165 A1 | 1/2013 |
| WO | 2013/010184 A1 | 1/2013 |
| WO | 2013/006724 A3 | 4/2013 |
| WO | 2014/179454 A1 | 11/2014 |
| WO | 2014/179459 A2 | 11/2014 |
| WO | 2014/179459 A3 | 1/2015 |
| WO | 2015/013271 A1 | 1/2015 |
| WO | 2015/013493 A1 | 1/2015 |
| WO | 2015/013574 A1 | 1/2015 |

OTHER PUBLICATIONS

Cuculich P.S., et al., "The Electrophysiological Cardiac Ventricular Substrate in Patients After Myocardial Infection" J Am Coll Cardiol 2011; 58: 1893-1902.

Medtronic Vitatron Carelink Encore® Programmer Model 29901 Reference Manual, 2013, Medtronic, Inc. Minneapolis, MN.

(PCT/US2014/047611) PCT Notification of Transmittal of the International Search Report and the Written Opinion of the International Searching Authority.

(PCT/US2014/047583) PCT Notification of Transmittal of the International Search Report and the Written Opinion of the International Searching Authority.

(PCT/US2014/047611) PCT Notification of Transmittal of the International Search Report and the Written Opinion of the International Searching Authority, Published Dec. 18, 2014, Filed Jun. 13, 2014.

U.S. Appl. No. 14/220,733, filed Mar. 20, 2014, Ghosh et al.

International Search Report and Written Opinion issued May 3, 2012 for International Application No. PCT/US2012/036262; 9 pages.

International Search Report and Written Opinion issued May 3, 2012 for International Application No. PCT/US2012/036302; 9 pages.

International Search Report and Written Opinion issued Aug. 6, 2014 for International Application No. PCT/US2014/036153; 14 pages.

International Search Report and Written Opinion issued Nov. 7, 2014 for International Application No. PCT/US2014/036163; 12 pages.

International Search Report and Written Opinion issued Oct. 28, 2014 for International Application No. PCT/US2014/041928; 15 pages.

(56) References Cited

OTHER PUBLICATIONS

International Search Report and Written Opinion issued Oct. 24, 2014 for International Application No. PCT/US2014/041929; 14 pages.

International Search Report and Written Opinion issued on Mar. 9, 2015 for International Application No. PCT/US2014/069214; 11 pages.

International Search Report and Written Opinion issued on Mar. 17, 2015, for International Application No. PCT/US2014/069192; 11 pages.

International Search Report and Written Opinion issued on Mar. 16, 2015 for International Application No. PCT/US2014/069182; 11 pages.

International Search Report and Written Opinion issued on Apr. 8, 2015 for International Application No. PCT/US2014/069070; 11 pages.

Biffi et al., "Occurrence of Phrenic Nerve Stimulation in Cardiac Resynchronization Therapy Patients: the Role of Left Ventricular Lead Type and Placement Site," *Europace*, 2013; 15:77-82.

"CardioGuide System Enables Real-Time Navigation of Left Ventricular Leads During Medtronic CRT Implants," Press Release, Apr. 9, 2013, Medtronic, Inc., 2 pgs.

Czerwinska et al., "Method of Segmentation of Thorax Organs Images Applied to Modeling the Cardiac Electrical Field," *Engineering in Medicine and Biology Society*, Proceedings of the 22$^{nd}$ Annual International Conference of the IEEE, vol. 1, 23, Jul. 23, 2000.; pp. 402-405.

Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.

Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.

Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.

Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.

Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.

Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.

Hayes et al., "Cardiac Resynchronization Therapy and the Relationship of Percent Biventricular Pacing to Symptoms and Survival," *Heart Rhythm*, Sep. 2011; 8(9):1469-1475.

"Heart Failure Management" datasheet [online]. Medtronic, Minneapolis, Minnesota, [Last updated on Jun. 3, 2013]. Retrieved from the Internet: www.medtronic.com; 9 pages.

Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.

Kornreich, "Body Surface Potential Mapping of ST Segment Changes in Acute Myocardial Infarction," *Circulation*, 1993; 87: 773-782.

Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.

Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-222.

Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.

Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.

Sperzel et al., "Intraoperative Characterization of Interventricular Mechanical Dyssynchrony Using Electroanatomic Mapping System—A feasibility Study," *Journal of Interventional Cardiac Electrophysiology*, Nov. 2012; 35(2):189-96.

Steinhaus BM., "Estimating cardiac transmembrane activation and recovery times from unipolar and bipolar extracellular electrograms: a simulation study," Circulation Research, 1989, 64:449-462.

Sweeney et al., "Analysis of Ventricular Activation Using Surface Electrocardiography to Predict Left Ventricular Reverse Volumetric Remodeling During Cardiac Resynchronization Therapy," *Circulation*, Feb. 9, 2010; 121(5):626-634.

Turner et al, "Electrical and Mechanical Components of Dyssynchrony in Heart Failure Patients with Normal QRS Duration and Left Bundle-Branch Block," *Circulation* 2004; 109: 2544-2549.

van Deursen et al., "Vectorcardiography as a Tool for Easy Optimization of Cardiac Resynchronization Therapy in Canine Left Bundle Branch Block Hearts," *Circulation Arrhythmia and Electrophysiology*, Jun. 1, 2012; 5(3):544-552.

Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.

Varma et al., "Placebo CRT," Journal of Cardiovascular Electrophysiology, vol. 19, Aug. 2008; p. 878.

Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.

International Search Report and Written Opinion for PCT/US2014/0247583, issued Nov. 4, 2014; 7 pages.

International Search Report and Written Opinion issued on Nov. 12, 2014 for International Application No. PCT/US2014/047971; 7 pages.

International Search Report and Written Opinion issued on Nov. 12, 2014 for International Application No. PCT/US2014/048120; 7 pages.

International Search Report and Written Opinion issued on Jun. 11, 2015 for International Application No. PCT/US2015/021442; 13 pages.

Ghosh et al., "Electrophysiological Substrate and Intraventricular LV Dyssynchrony in Non-ischemic Heart Failure Patients Undergoing Cardiac Resynchronization Therapy," *Heart rhythm: the official journal of the Heart Rhythm Society*, 2011; 8(5):692-699.

Potse et al., "Mathematical Modeling and Simulation of Ventricular Activation Sequences: Implications for Cardiac Resynchronization Therapy," *J. of Cardiovasc. Trans. Res.*, 2012; 5:146-158.

Prinzen et al., "Cardiac Resynchronization Therapy State-of-the-Art of Current Applications, Guidelines, Ongoing Trials, and Areas of Controversy" *Circulation*, 2013; 128: 2407-2418.

Strik et al., "Electrical and Mechanical Ventricular Activation During Left Bundle Branch Block and Resynchronization," *J. of Cardiovasc. Trans. Res.*, 2012; 5:11-126.

IDENTIFICATION OF HEALTHY VERSUS UNHEALTHY SUBSTRATE FOR PACING FROM A MULTIPOLAR LEAD

TECHNICAL FIELD

The disclosure relates generally to identifying the presence of healthy versus unhealthy cardiac substrate and particularly a system and method for identifying substrate for receiving cardiac pacing.

BACKGROUND

Myocardial ischemia or myocardial infarction can produce areas of scar tissue in the myocardial substrate that will be unresponsive to cardiac pacing. If a patient having myocardial scar tissue requires cardiac pacing, the location of the scar tissue is preferably avoided in positioning pacing electrodes. However, the location of the scar tissue may be unknown without performing imaging procedures, such as magnetic resonance imaging (MRI), which may be costly, require catheterization or contrast agents, and may not be readily available in some geographic areas.

Cardiac resynchronization therapy (CRT) is one type of cardiac pacing therapy that is used as a treatment for heart failure patients in which one or more heart chambers are electrically stimulated (paced) to restore or improve heart chamber synchrony. Achieving a positive clinical benefit from CRT is dependent on several therapy control parameters including selection of pacing site(s) and the relative timing of pacing pulses delivered in the right and/or left ventricles. For example, selection of a CRT pacing site that avoids myocardial scar tissue is important in achieving clinical benefit. Systems and methods are needed for identifying myocardial scar tissue versus healthy myocardial substrate at a potential pacing site in a patient receiving CRT or other pacing therapy without requiring costly imaging technology.

SUMMARY

In general, the disclosure is directed towards techniques for determining presence of scar tissue. In one embodiment, a method determines the presence of scar tissue by a processing device receiving a torso-surface potential signal from multiple electrodes distributed on a torso of a patient. Features of the potential signal from each of the plurality of electrodes are extracted and stored in a non-transitory storage medium. A scar indicator index is determined for each of the electrodes from the stored features. The electrodes having an affirmative scar indicator index are identified, and an overall scar burden index is determined as a proportion of the electrodes with an affirmative scar indicator index.

In another embodiment, a medical device system for determining presence of scar tissue includes a processor receiving means for receiving a torso-surface potential signal from each of multiple electrodes distributed on a torso of a patient and processor means for extracting features of the potential signal from each of the plurality of electrodes. The features are stored, and a processor determines a scar indicator index for each of the electrodes from the stored features, identifies electrodes having an affirmative scar indicator index, and determines an overall scar burden index as a proportion of the electrodes with an affirmative scar indicator index.

In another embodiment, a non-transitory, computer readable storage medium stores instructions for causing a processor of a medical device system to perform a method for determining presence of myocardial scar tissue. The method includes receiving a torso-surface potential signal from electrodes distributed on a torso of a patient, extracting features of the potential signal from each of the electrodes, storing values of the features in a non-transitory storage medium, determining a scar indicator index for each of the electrodes from the stored features, identifying electrodes having an affirmative scar indicator index, and determining an overall scar burden index as a proportion of the electrodes with an affirmative scar indicator index.

Other embodiments and aspects of a system and method for determining presence of scar tissue are described herein. The details of one or more aspects of the disclosure are set forth in the accompanying drawings and the description below.

Other features, objects, and advantages will be apparent from the description and drawings, and from the claims.

DETAILED DESCRIPTION

Figure 1:
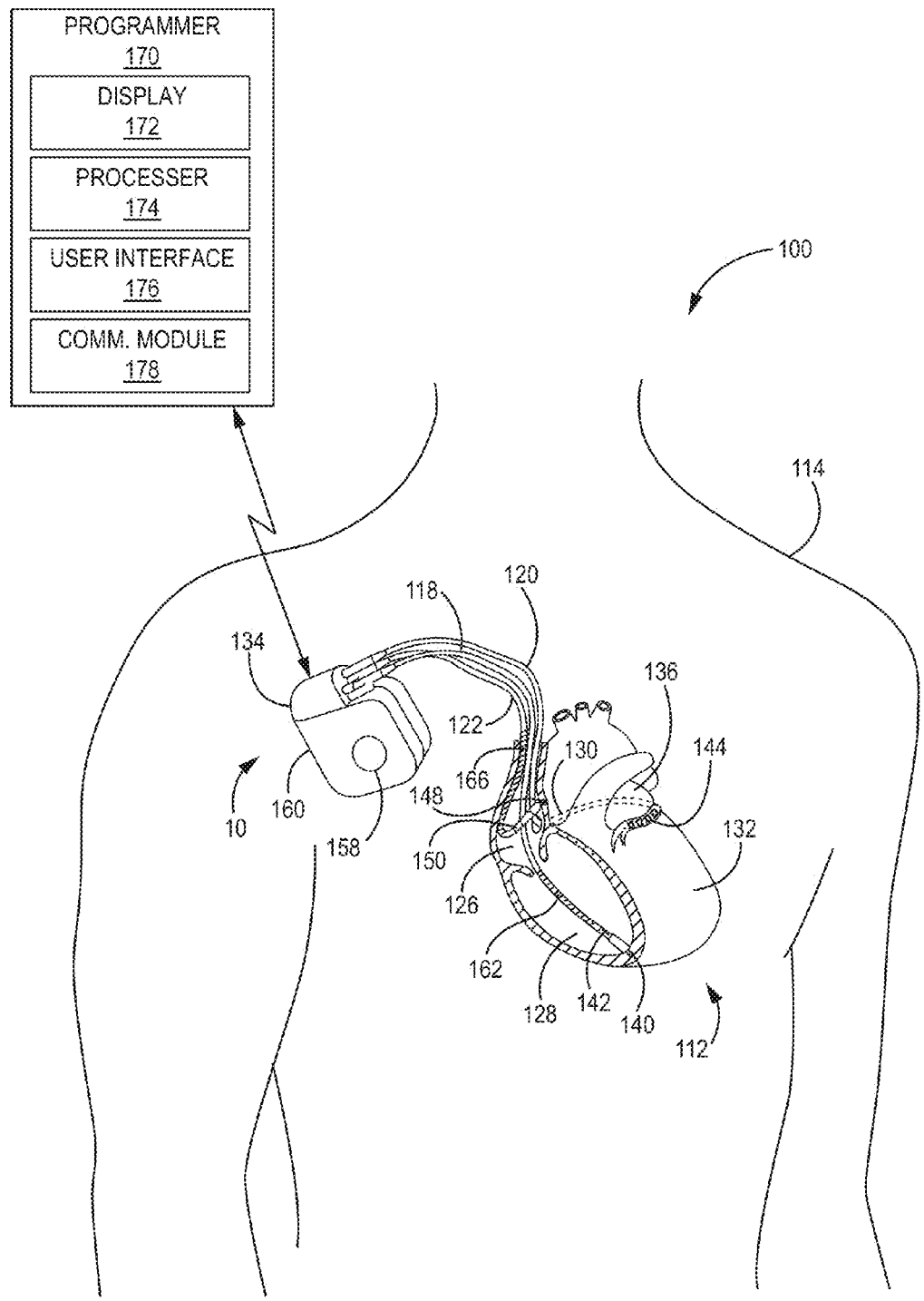
FIG. 1 is a schematic diagram of one embodiment of an implantable medical device (IMD) system in which techniques disclosed herein may be implemented to provide therapy to a heart of a patient.

FIG. 1 is a schematic diagram of one embodiment of an implantable medical device (IMD) system 100 in which techniques disclosed herein may be implemented to provide therapy to heart 112 of patient 114. System 100 includes IMD 10 coupled to leads 118, 120, and 122 which carry multiple electrodes. IMD 10 is configured for bidirectional communication with programmer 170. IMD 10 may be, for example, an implantable pacemaker or implantable cardioverter defibrillator (ICD) that provides electrical signals to heart 112 via electrodes coupled to one or more of leads 118, 120, and 122 for pacing, cardioverting and defibrillating the heart 112. IMD 10 is capable of delivering pacing in one or more heart chambers, and in the embodiment shown, is configured for multi-chamber pacing and sensing in the right atrium (RA) 126, the right ventricle (RV) 128, and the left ventricle (LV) 132 using leads 118, 120 and 122.

IMD 10 delivers RV pacing pulses and senses RV intracardiac electrogram (EGM) signals using RV tip electrode 140 and RV ring electrode 142. RV lead 118 is shown to carry a coil electrode 162 which may be used for delivering high voltage cardioversion or defibrillation shock pulses. IMD 10 senses LV EGM signals and delivers LV pacing pulses using the electrodes 144 carried by a multipolar coronary sinus lead 120, extending through the RA 126 and into a cardiac vein 130 via the coronary sinus. In some embodiments, coronary sinus lead 120 may include electrodes positioned along the left atrium (LA) 136 for sensing left atrial (LA) EGM signals and delivering LA pacing pulses.

IMD 10 senses RA EGM signals and delivers RA pacing pulses using RA lead 122, carrying tip electrode 148 and ring electrode 150. RA lead 122 is shown to be carrying coil electrode 166 which may be positioned along the superior vena cava (SVC) for use in delivering cardioversion/defibrillation shocks. In other embodiments, RV lead 118 carries both the RV coil electrode 162 and the SVC coil electrode 166. IMD 10 may detect tachyarrhythmias of heart 112, such as fibrillation of ventricles 128 and 132, and deliver high voltage cardioversion or defibrillation therapy to heart 112 in the form of electrical shock pulses. Pacing and sensing of the cardiac chambers is typically achieved using the pace/sense electrodes 140, 142, 144, 148 and 150, however in some embodiments coil electrodes 162 and/or 166 may be used in sensing and/or pacing electrode vectors.

While IMD 10 is shown in a right pectoral implant position in FIG. 1, a more typical implant position, particularly when IMD 10 is embodied as an ICD, is a left pectoral implant position. In other embodiments, IMD 10 may be implanted in an abdominal location.

IMD 10 includes internal circuitry for performing the functions attributed to IMD 10. Housing 160 encloses the internal circuitry. It is recognized that the housing 160 or portions thereof may be configured as an active electrode 158 for use in cardioversion/defibrillation shock delivery or used as an indifferent electrode for unipolar pacing or sensing configurations with any electrodes carried by leads 118, 120 and 122. IMD 10 includes a connector block 134 having connector bores for receiving proximal lead connectors of leads 118, 120 and 122. Electrical connection of electrodes carried by leads 118, 120 and 122 and IMD internal circuitry is achieved via various connectors and electrical feedthroughs included in connector block 134.

IMD 10 is configured for delivering CRT by delivering pacing pulses in one or both ventricles 128 and 132 for controlling and improving ventricular synchrony. LV pacing may be delivered using a selected pacing vector that utilizes at least one electrode 144 on multipolar LV lead 120. RV pacing is delivered using RV tip electrode 140 and ring electrode 142. CRT may be delivered by pacing in a single ventricular chamber (LV or RV) or both chambers (biventricular pacing) depending on patient need. The methods described herein are implemented in a dual or multi-chamber pacemaker or ICD delivering pacing pulses to the right and/or left ventricles using programmable pacing pulse timing parameters and selected pacing sites and pacing vectors.

While a multi-chamber ICD is shown in FIG. 1, it is recognized that techniques disclosed herein may be implemented in a single chamber, dual chamber or multi-chamber pacemaker, with or without anti-arrhythmia therapies such as cardioversion and defibrillation shock capabilities. For example, techniques disclosed herein for identifying pacing site(s) for CRT may be used for guiding selection of a pacing site for any pacing therapy by identifying myocardial scar tissue at a potential pacing site.

Programmer 170 includes a display 172, a processor 174, a user interface 176, and a communication module 178 including wireless telemetry circuitry for communication with IMD 10. In some examples, programmer 170 may be a handheld device or a microprocessor-based home monitor or bedside programming device. A user, such as a physician, technician, nurse or other clinician, may interact with programmer 170 to communicate with IMD 10. For example, the user may interact with programmer 170 via user interface 176 to retrieve currently programmed operating parameters, physiological data collected by IMD 10, or device-related diagnostic information from IMD 10. A user may also interact with programmer 170 to program IMD 10, e.g., select values for operating parameters of the IMD. A user interacting with programmer 170 can initiate a test to identify scar tissue at a potential pacing site according to the techniques disclosed herein. As will be described, in a test to identify scar tissue, a multi-polar lead is used to record multiple unipolar EGM signals, determine a combination of EGM signal features from each of the EGM signals, and analyze the combination of EGM signal features to detect scar tissue at an electrode site.

Programmer 170 includes a communication module 178 to enable wireless communication with IMD 10. Examples of communication techniques used by system 100 include low frequency or radiofrequency (RF) telemetry, which may be an RF link established via Bluetooth, WiFi, or MICS for example. In some examples, programmer 170 may include a programming head that is placed proximate to the patient's body near the IMD 10 implant site, and in other examples programmer 170 and IMD 10 may be configured to communicate using a distance telemetry algorithm and circuitry that does not require the use of a programming head and does not require user intervention to maintain a communication link.

It is contemplated that programmer 170 may be coupled to a communications network via communications module 178 for transferring data to a remote database or computer to allow remote monitoring and management of patient 114 using the techniques described herein. Remote patient management systems may be configured to utilize the presently disclosed techniques to enable a clinician to review test data, programmed therapy parameters and authorize programming of IMD 10. Reference is made to commonly-assigned U.S. Pat. Nos. 6,599,250 (Webb et al.), 6,442,433 (Linberg et al.), 6,418,346 (Nelson et al.), and 6,480,745 (Nelson et al.) for general descriptions and examples of network communication systems for use with implantable medical devices for remote patient monitoring and device programming, all of which patents are hereby incorporated herein by reference in their entirety.

Figure 2:
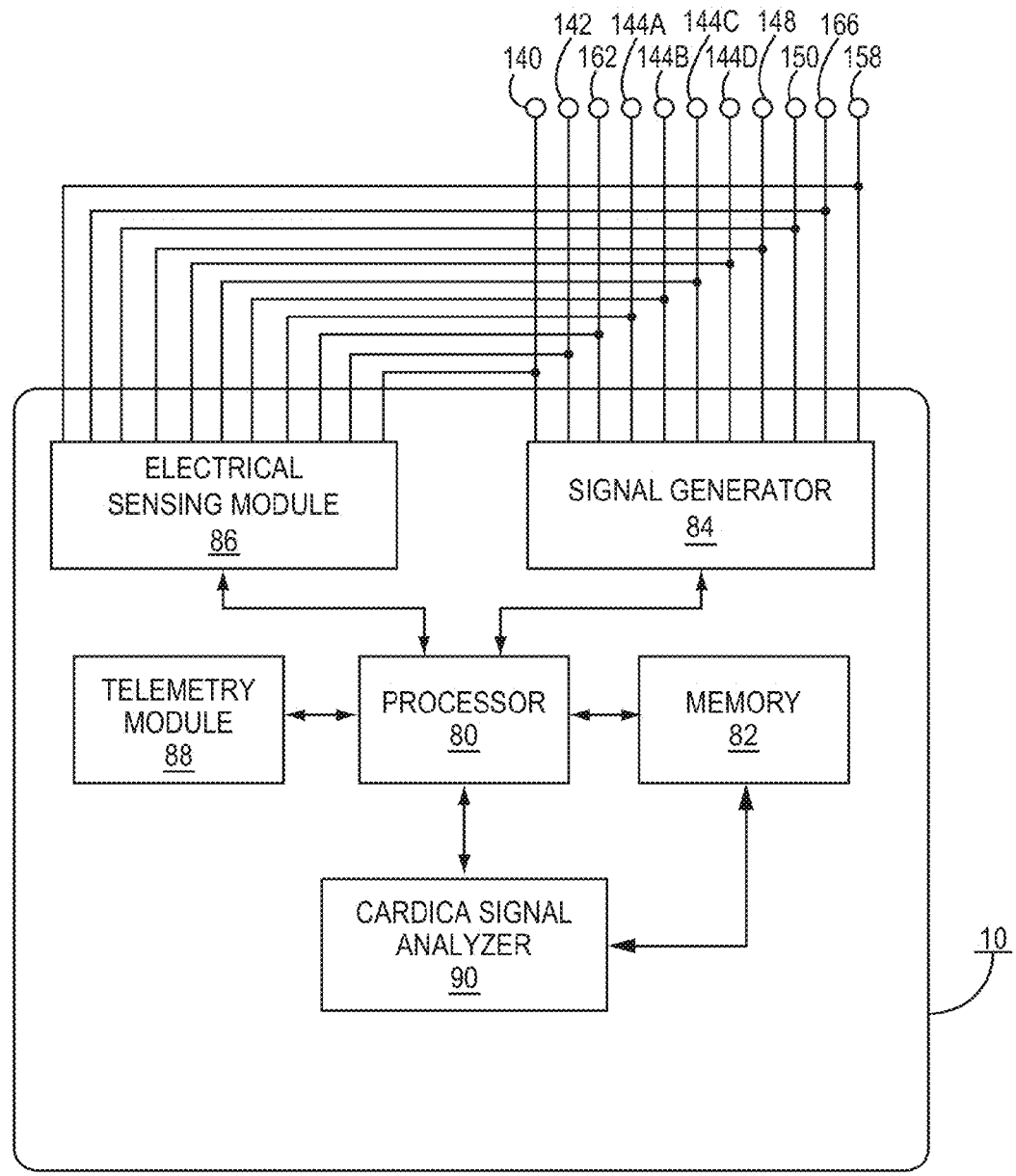
FIG. 2 is a functional block diagram illustrating one example configuration of an IMD.

FIG. 2 is a functional block diagram illustrating one example configuration of IMD 10. In the example illustrated by FIG. 2, IMD 10 includes a processor and control unit 80, also referred to herein as "processor" 80, memory 82, signal generator 84, electrical sensing module 86, and telemetry module 88. IMD 10 further includes cardiac signal analyzer 90.

Memory 82 may include computer-readable instructions that, when executed by processor 80, cause IMD 10 and processor 80 to perform various functions attributed throughout this disclosure to IMD 10, processor 80, and cardiac signal analyzer 90. The computer-readable instructions may be encoded within memory 82. Memory 82 may comprise non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media with the sole exception being a transitory propagating signal.

Processor and control unit 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. In one example, cardiac signal analyzer 90 may, at least in part, be stored or encoded as instructions in memory 82 that are executed by processor and control unit 80.

Processor and control unit 80 includes a therapy control unit that controls signal generator 84 to deliver electrical stimulation therapy, e.g., cardiac pacing or CRT, to heart 112 according to a selected one or more therapy programs, which may be stored in memory 82. Signal generator 84 is electrically coupled to electrodes 140, 142, 144A-144D (collectively 144), 148, 150, 158, 162, and 166 (all of which are shown in FIG. 1), e.g., via conductors of the respective leads 118, 120, 122, or, in the case of housing electrode 158, via an electrical conductor disposed within housing 160 of IMD 10. Signal generator 84 is configured to generate and deliver electrical stimulation therapy to heart 112 via selected combinations of electrodes 140, 142, 144, 148, 150, 158, 162, and 166. Signal generator 84 delivers cardiac pacing pulses according to therapy control parameters during CRT. CRT is delivered to a pacing site identified as not being over scar tissue as will be described herein.

Signal generator 84 may include a switch module (not shown) and processor and control 80 may use the switch module to select, e.g., via a data/address bus, which of the available electrodes are used to deliver pacing pulses. Processor 80 controls which of electrodes 140, 142, 144A-144D, 148, 150, 158, 162, and 166 is coupled to signal generator 84 for delivering stimulus pulses, e.g., via the switch module. The switch module may include a switch array, switch matrix, multiplexer, or any other type of switching device suitable to selectively couple a signal to selected electrodes.

Sensing module 86 monitors cardiac electrical signals for sensing cardiac electrical events, e.g. P-waves and R-waves, from selected ones of electrodes 140, 142, 144A-144D, 148, 150, 158, 162, or 166 in order to monitor electrical activity of heart 112. Sensing module 86 may also include a switch module to select which of the available electrodes are used to sense the cardiac electrical activity. In some examples, processor 80 selects the electrodes to function as sense electrodes, or the sensing vector, via the switch module within sensing module 86.

Sensing module 86 includes multiple sensing channels, each of which may be selectively coupled to respective combinations of electrodes 140, 142, 144A-144D, 148, 150, 158, 162, or 166 to detect electrical activity of a particular chamber of heart 112. Each sensing channel may comprise an amplifier that outputs an indication to processor 80 in response to sensing of a cardiac depolarization, in the respective chamber of heart 112. In this manner, processor 80 may receive sense event signals corresponding to the occurrence of R-waves and P-waves in the various chambers of heart 112, e.g. ventricular sense events and atrial sense events corresponding to intrinsic depolarization of the respective heart chamber. Sensing module 86 may further include digital signal processing circuitry for providing processor 80 or cardiac signal analyzer 90 with digitized EGM signals.

In various embodiments, one or more sensing channels may be selectively coupled to electrodes 144 included on multipolar lead 120 for sensing unipolar EGM signals for detecting scar tissue. In one embodiment, sensing module 86 includes an LV sensing channel and electrodes 144a, 144b, 144c and 144d are selectively coupled one at a time in a unipolar sensing configuration in combination with a common anode, such as housing electrode 158, coil electrode 162, or coil electrode 166, to acquire a unipolar EGM signal for each of the respective locations of electrodes 144a-144d along LV tissue.

A digitized EGM signal obtained using each of the electrodes 144a-144d is analyzed by cardiac signal analyzer 90 to extract a combination of EGM signal features, e.g. at least two features, from each of the unipolar sensed signals. The extracted features are analyzed to detect scar tissue as will be described in greater detail below. In response to detecting scar tissue, processor 80 may generate a notification for transmission via telemetry module 88 and/or establish or alter a pacing electrode selection for delivering CRT therapy. Processor 80 and cardiac signal analyzer 90 may collectively represent processor means for determining the presence of scar tissue as described herein.

Memory 82 stores intervals, counters, or other data used by processor 80 to control the delivery of pacing pulses by signal generator 84. Such data may include intervals and counters used by processor 80 to control the delivery of pacing pulses to one or both of the left and right ventricles for CRT. The intervals and/or counters are, in some examples, used by processor 80 to control the timing of delivery of pacing pulses relative to an intrinsic or paced event in another chamber.

Other examples of functional block diagrams of IMD 10 may be seen with respect to U.S. patent application Ser. No. 13/916,353 (e.g., FIGS. 17A-17B) filed Jun. 12, 2013, and assigned to the assignee of the present invention, the disclosure of which is incorporated by reference in its entirety herein.

Figure 3:
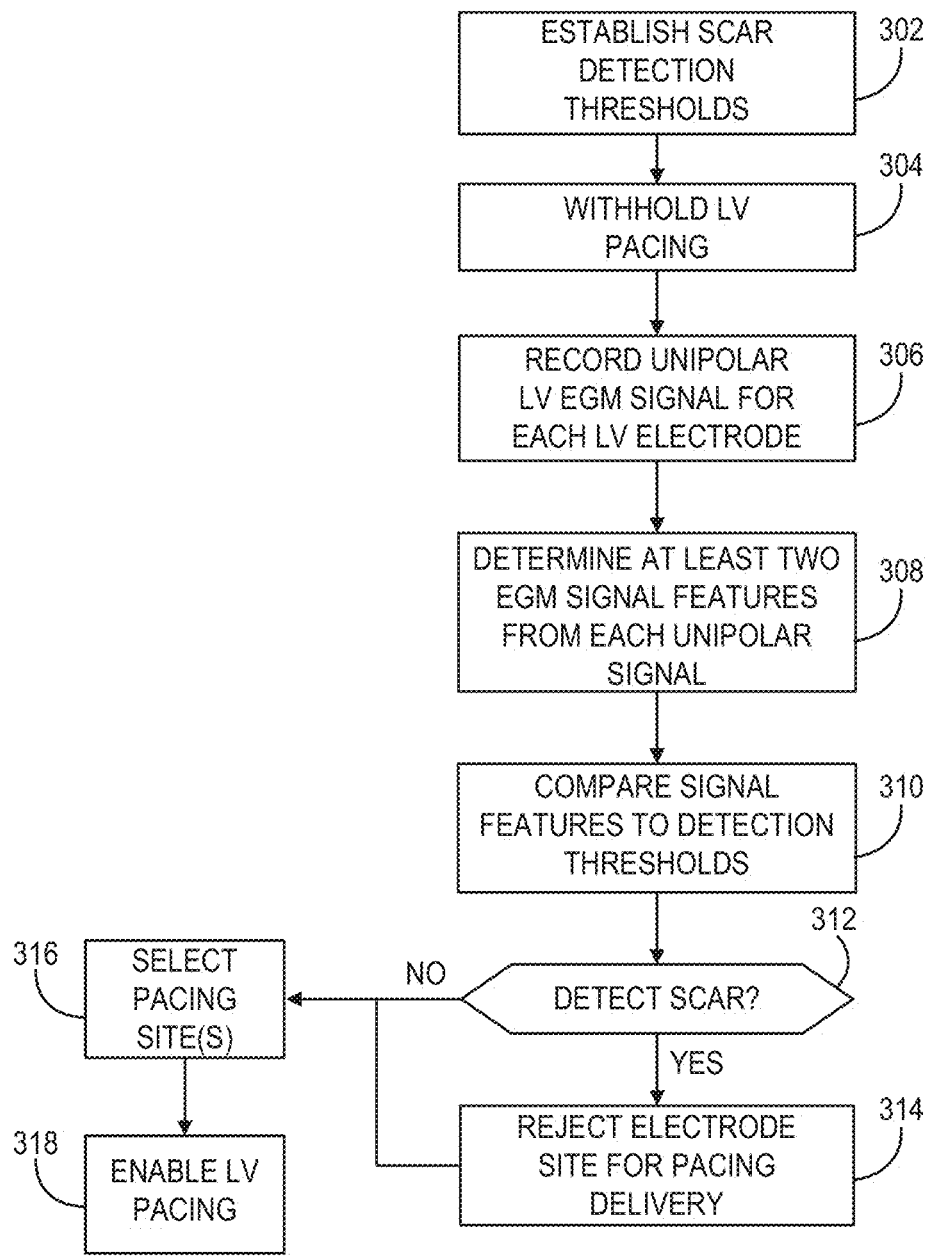
FIG. 3 is a flow chart of a method for detecting myocardial scar tissue according to one embodiment.

FIG. 3 is a flow chart 300 of one method for detecting myocardial scar tissue according to one embodiment. The method described in conjunction with FIG. 3 is directed to the illustrative embodiment shown in FIG. 1 of an IMD 10 coupled to a quadripolar lead having four electrodes 144A-144D positioned along the LV for delivering LV pacing pulses during CRT. It is recognized, however, that the techniques disclosed herein may be utilized in a variety of embodiments that include multiple electrodes positioned along a heart chamber carried by one or more medical electrical leads.

When multiple electrodes are available, conventional "short" bipolar pairs that enable recording of a true, near-field bipolar signal can be used to detect myocardial scar tissue by detecting changes in the bipolar EGM signal due to changes in the local, near-field EGM signal. However, as the distance between the sensing pair of electrodes increases, the volume of tissue contributing to the recorded EGM signal will increase. More far-field electrical activity will be contributing to the recorded signal reducing the sensitivity of the signal to detecting scar tissue at the sensing electrode site. A multipolar lead may provide multiple sensing/pacing sites, however the spacing between electrodes along the multipolar lead may be greater than that required to record a bipolar signal with great enough sensitivity to reliably detect EGM signal changes caused by scar tissue. The process shown by flow chart 300 provides a technique for detecting the presence of scar tissue at an electrode site independent of inter-electrode spacing when multiple electrodes are positioned at various sites along a heart chamber.

The process shown by flow chart 300 may be performed at the time an IMD and associated leads are being initially implanted, at a time of repositioning or replacing a cardiac lead, on a periodic basis after implanting the IMD and associated leads. In some embodiments, the process shown by flow chart 300 may be performed in response to a change in a monitored parameter, such as a change in a hemodynamic parameter or a change in a pacing capture threshold.

At block 302, scar tissue detection thresholds are established. Thresholds for detecting scar may be based on previous EGM baseline recordings obtained from the patient, EGM recordings obtained from the patient at the time the test for detecting scar is being performed, or based on empirical data from a population of patients. Thresholds are applied to at least two EGM signal features determined from each unipolar EGM signal. Separate thresholds may be applied to each of the two or more EGM signal features individually or to a single metric or index computed from the two or more EGM signal features and a single threshold applied to the metric.

At block 304, LV pacing is withheld. EGM signals for the purposes of detecting myocardial scar tissue in the LV are recorded during a baseline rhythm which typically does not involve pacing from the LV lead or electrodes. The heart rhythm may be an intrinsic heart rhythm with no pacing delivered in any heart chamber, an atrial paced rhythm, an RV paced rhythm, or during pacing in an atrial chamber and the RV. It is contemplated that in some cases another LV lead or electrode may be present different than the pacing electrodes and associated sites being tested for scar tissue that could be used for pacing during recording of unipolar EGM signals at the LV pacing sites under test.

At block 306, unipolar LV EGM signals are recorded by sensing module 86 for each LV electrode 144a-d available when no LV pacing is being delivered. The LV EGM signals are recorded using a common anode paired with each LV electrode for sensing n different unipolar EGM signals when n electrodes are positioned along the LV. The different unipolar EGM signals may be recorded one at a time in a sequential manner or simultaneously depending on the number of sensing channels available in the sensing module 86 IMD 10. Each unipolar signal may be recorded for at least one cardiac cycle and generally will be recorded for multiple cycles, e.g. 3 to 12 cycles, for obtaining representative EGM signal features from for a given sensing electrode site.

At block 308, at least two different EGM signal features are extracted from each recorded unipolar signal. At least two different signal features are extracted in case a single feature of the unipolar EGM does not provide a great enough sensitivity to reliably detect EGM signal changes due to scar tissue. The signal features extracted from each unipolar EGM signal may include, but are not limited to, metrics of the QRS amplitude, negativity of the Q-wave, and fractionation of the EGM signal. It is recognized that numerous techniques can be conceived for determining a metric of QRS signal amplitude, a metric of Q-wave negativity, and a metric of QRS fractionation.

For the sake of illustration, a metric of QRS amplitude may be determined as the peak-to-peak amplitude difference during a QRS sensing window. The QRS amplitude is expected to be reduced when scar tissue is present at the sensing electrode as compared to healthy tissue at the sensing electrode.

A broad negative Q-wave is also evidence of scar tissue. A metric of Q-wave negativity can be extracted from the EGM signal by counting the number of digitized EGM sample points that are negative during a QRS sensing window, by determining a summation of EGM sample point values over a QRS sensing window, or by determining an integral or area defined by the EGM signal sample points over a sensing window.

Scar tissue may also cause fractionation of the EGM signal, i.e. multiple peaks rather than a single R-wave peak. A metric of fractionation of the EGM signal may be extracted from the EGM signal by counting a number of slope sign changes, counting a number of peaks, or counting a number of inflection points during a QRS sensing window.

In one embodiment, at least two metrics of QRS amplitude, Q-wave negativity, and/or EGM fractionation are determined from each unipolar EGM signal at block 308. These metrics are compared to the established detection thresholds at block 310, individually and/or in a combined metric. Criteria may be defined for detecting scar tissue. For example, at least two out of three EGM signal features must meet a respective scar detection threshold to detect scar tissue at a sensing electrode site. If scar detection threshold(s)/criteria are satisfied at block 312, the electrode used to record the associated EGM signal is rejected as a pacing site at block 314.

At block 316, pacing site(s) for delivering pacing therapy are selected. Any electrodes available after rejecting those electrodes associated with scar detection may be selected for therapy delivery and additional pacing site selection criteria may be applied to select a pacing site according to the particular pacing application. Pacing site selection may be performed automatically at block 316 by rejecting any electrodes identified as being located along scar tissue and applying any other therapy pacing site selection criteria, e.g. low capture threshold, low impedance etc. Pacing site selection may alternatively be performed by a clinician after transmitting a notification to an external programmer or other device that scar has been detected and indicating the associated electrode(s). At block 318, LV pacing is enabled such that a desired therapy can be delivered according to programmed therapy control parameters at the selected pacing site(s).

Figure 4:
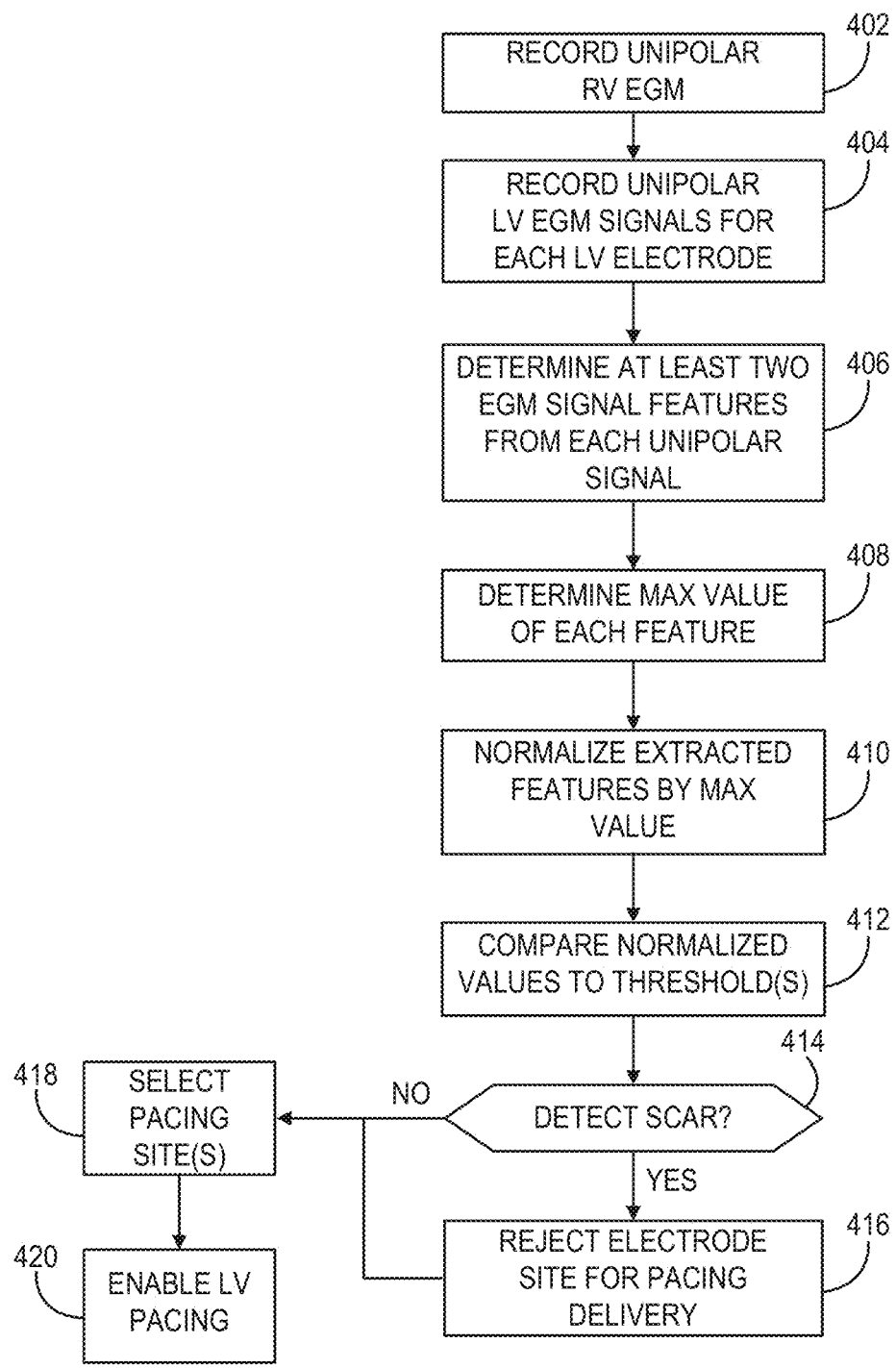
FIG. 4 is a flow chart of a method for extracting unipolar EGM signal features for detecting scar tissue according to one embodiment.

FIG. 4 is a flow chart 400 of a method for extracting unipolar EGM signal features for detecting scar tissue according to one embodiment. At block 402, heart activity is sensed at an electrode positioned along the RV to produce a unipolar EGM waveform of RV heart activity. The RV unipolar EGM signal is recorded during an intrinsic rhythm or during atrial pacing, while no RV pacing is being delivered.

At block 404, heart activity is sensed at each electrode positioned along the LV to produce unipolar EGM waveforms corresponding to each LV electrode site. At least two features are extracted from each of the RV and LV unipolar EGM waveforms at block 406. The extracted EGM features are representative of the heart activity at the associated electrode site and may include a metric of QRS waveform amplitude, a metric of Q-wave negativity, and a metric of QRS waveform fractionation. In an illustrative embodiment, one feature extracted from the unipolar EGM waveform is a peak-to-peak amplitude difference as a metric of QRS amplitude. In another embodiment, one extracted feature is a percentage of the EGM waveform sample points having a negative polarity out of all of the EGM waveform sample points during the QRS sensing window as a metric of Q-wave negativity. In yet another embodiment, one extracted feature is a number of times the slope of the EGM waveform changes between a positive slope and a negative slope (in either direction) as a metric of fractionation of the QRS signal. Any combination of at least two features of the EGM waveform may be extracted.

The features may be extracted by first setting a QRS window. The QRS window is centered at an R-wave sensed by a sense amplifier included in the IMD sensing module in one embodiment and extends a predetermined time interval earlier and later than the R-wave sense marker generated by the sense amplifier. The EGM features may then be extracted from the waveform sample points during the window. A given feature may be extracted on a beat-by-beat basis for a predetermined number of beats and then averaged to determine an average feature representative of heart activity at the electrode site or a median or mode of the extracted features may be determined. Alternatively, the EGM waveform may be ensemble averaged over the QRS window for multiple beats then a feature can be extracted from the averaged QRS waveform.

The features are determined for each unipolar EGM signal recorded, and at block 408 a maximum of an EGM feature determined from all recorded signals is identified. The maximum value, which may be an absolute value, of a given EGM feature is used to normalize the given EGM feature values extracted from each unipolar EGM waveform at block 410. In this way, a percentage difference in a feature value is determined relative to a maximum feature value. For example, if a unipolar EGM signal has a normal peak-to-peak amplitude difference and another unipolar EGM signal has a normalized peak-to-peak amplitude that is 50% of the normal peak-to-peak amplitude, the 50% lower peak-to-peak amplitude is a signal feature indicating scar tissue at the associated electrode site. One or more extracted features may be normalized by a maximum and compared to a threshold percentage for identifying scar tissue at block 412. It is recognized that in some cases, feature values may be normalized by a minimum feature value, a mean feature value or other reference value. In some examples, a value used to normalize extracted features values is extracted from the RV EGM.

A normalized or non-normalized value may indicate scar when the value exceeds a threshold percentage or level or is less than a threshold percentage or level depending on the particular feature. For example, a peak-to-peak amplitude difference may be normalized by a maximum and required to be less than a threshold percentage, e.g. 50%, while the percentage of negative sample points may be required to be greater than a threshold percentage. A number of slope changes may be left un-normalized and compared to a threshold number. In some embodiments, a threshold applied to the feature values extracted from the LV unipolar EGM signals is derived from the RV unipolar EGM signal.

If at least two extracted features of a unipolar EGM signal indicate scar tissue based on the detection threshold comparison, as determined at decision block 414, scar is detected at the associated electrode site. The electrode is rejected for use in delivering a pacing therapy at block 416 and/or a notification indicating detection of scar tissue and recommended rejection of the pacing site may be generated. Pacing site(s) may be selected at block 418 from electrodes that were not determined to be located along scar tissue and the pacing therapy may be enabled at block 420 using the selected pacing site(s). In this example, the selected pacing site is along the LV for delivering CRT.

Figure 5:
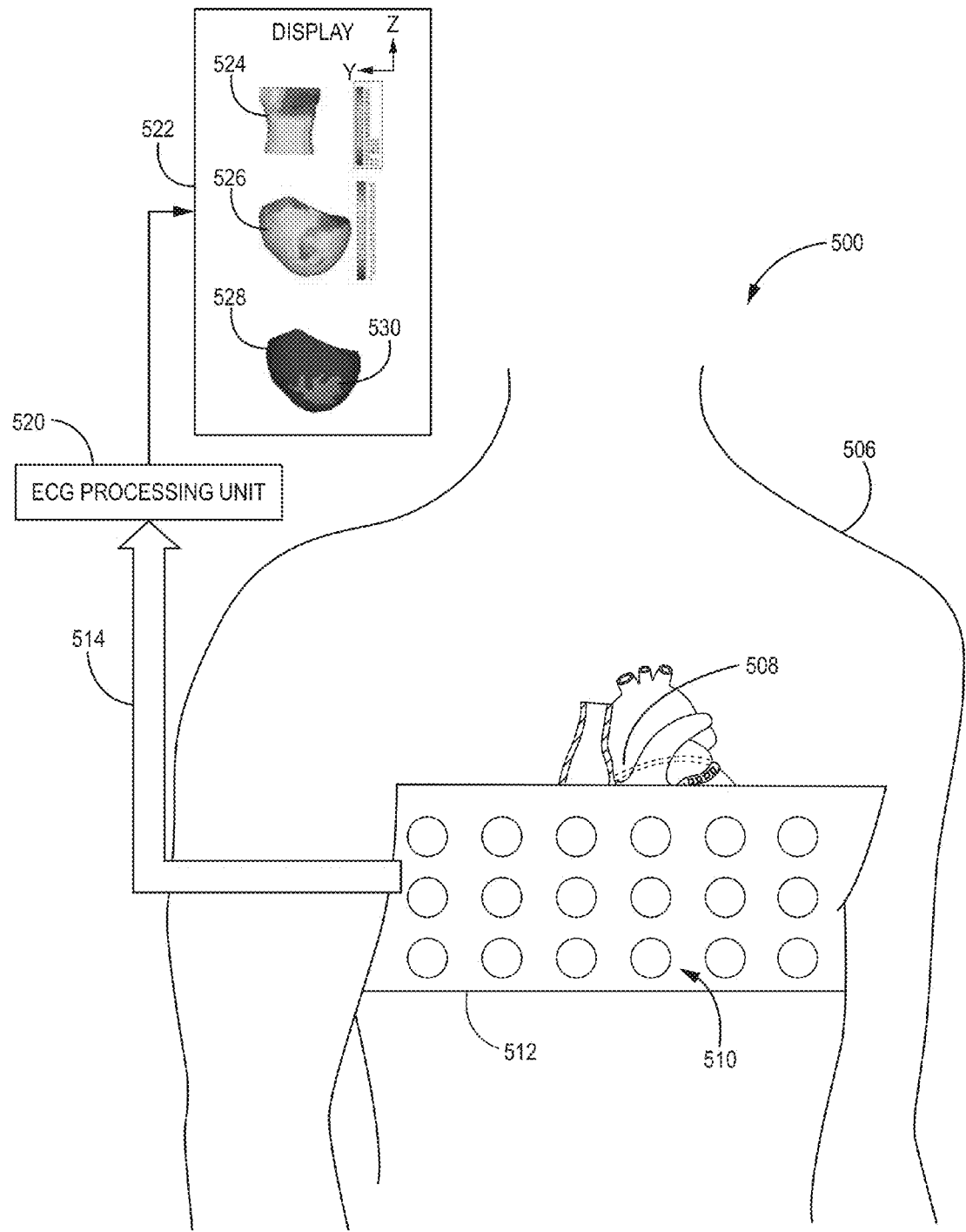
FIG. 5 is a schematic diagram of an external system for determining presence of scar tissue in a patient's heart.

FIG. 5 is a schematic diagram of an external system 500 for determining presence of scar tissue in a patient's heart. In some cases, an implanted lead may not be available for detecting EGM evidence of scar tissue or an implanted electrode may not be located to produce an EGM signal sensitive enough to reliably detect scar tissue. In these situations, a system and method for determining the presence of scar tissue without requiring costly or complex imaging systems may be needed to determine if scar is present and provide some assessment relating to the relative size of the scar in a metric referred to herein as the "scar burden." By approximating a location of scar tissue and the scar burden, a clinician can make informed treatment decisions. For example, if a patient is a candidate for CRT, knowledge of the presence of scar and an estimate of the scar burden is useful to a clinician in prescribing CRT and in planning lead and electrode placement for delivering CRT.

System 500 includes external surface electrodes 510, shown carried by a wearable band or strap 512 for positioning the electrodes 510 in skin contact along the torso of a patient 506. Electrodes 510 may alternatively be adhesive skin electrodes. Electrodes 510 are positioned at multiple points along the patient's torso to record surface potential signals. The electrodes 510 may be equally distributed circumferentially around the patient's torso in one example.

In one embodiment, electrodes 510 are used to acquire surface potential signals from heart 508 by strap 512 wrapped around the torso of patient 506 such that the electrodes 510 surround heart 508. Electrodes 510 may be positioned around the circumference of patient 506, including the posterior, lateral, and anterior surfaces of the torso of patient 506. In other examples, electrodes 512 may be positioned on any one or more of the posterior, lateral, and anterior surfaces of the torso. Electrodes 510 may be electrically connected to an ECG processing unit 520 via a wired connection 514. Some configurations may use a wireless connection to transmit the signals sensed by electrodes 510 to ECG processing unit 520, e.g., as channels of data.

Although in the example of FIG. 5, strap 512 is shown carrying surface electrodes 510, in other examples any of a variety of mechanisms, e.g., tape or adhesives, may be employed to aid in the spacing and placement of electrodes 510 in a distributed manner along a patient's torso to surround heart 508. In some examples, strap 512 may include an elastic band, strip of tape, or cloth. In other examples, electrodes 510 may be placed individually on the torso of patient 506.

Electrodes 510 record the electrical signals associated with the depolarization and repolarization of heart 508. Each of electrodes 510 may be used in a unipolar configuration to sense the surface potentials that reflect cardiac electrical activity. ECG processing unit 520 may also be coupled to a return or indifferent electrode (not shown) which may be used in combination with each of electrodes 510 for unipolar sensing.

ECG processing unit 520 may record and analyze the surface potential signals, referred to generally herein as "ECG" signals, sensed by electrodes 510. Processing unit 520 may be configured to provide an output to a user indicating presence of scar tissue in heart 112. The user may make a diagnosis, prescribe CRT, position therapy devices, e.g., leads, or adjust or select treatment parameters based on the indicated scar tissue.

The strap 512 carrying electrodes 510 is one illustrative embodiment of an apparatus that is useful in recording surface ECG signals from which presence of scar tissue can be determined. Other surface cardiac signal recording apparatus may be used for acquiring cardiac signal data from which presence scar tissue can be determined. Other signal recording apparatus and techniques may include 12-lead ECG electrodes, a vest carrying an array of electrodes, and vectorcardiography.

The electrodes 510 are coupled to an ECG processing unit 520 via electrical conductors 514. ECG signals are received by ECG processing unit 520 which extracts ECG features from each received signal for producing an ECG feature map. ECG features may be extracted from each ECG signal recorded from electrodes 510 in a manner similar to the techniques described above for extracting unipolar EGM features. For example, a QRS amplitude metric, a Q-wave negativity metric, an ECG fractionation metric or any combination thereof may be determined from the surface ECG signals as scar indicator indices.

The ECG features are thereby used for determining scar indicator indices, individually or in a combined form, and are compared to a scar detection threshold by ECG processing unit 520 to determine if scar tissue is present at a myocardial tissue site. The ECG processing unit 520 reports if scar tissue is detected and reports a scar burden, e.g. via display screen/monitor 522 coupled to ECG processing unit. The ECG processing unit 520 may produce a graphical display 524 of a 2-dimensional or 3-dimensional model of the patient's torso superimposed with a color-coded mapping of the extracted ECG feature values projected onto the torso model based upon the electrode locations along the patient's torso.

In some embodiments, ECG processing unit 520 and display screen/monitor 522 may be implemented in an external programmer, such as programmer 170 shown in FIG. 1. A programmer, such as the CARELINK ENCORE® Programmer Model 29901, configured to receive signals from surface ECG electrodes is available from Medtronic, Inc., Minneapolis, Minn. The Medtronic CARELINK ENCORE® Programmer Model 29901 Reference Manual, 2013, is incorporated herein by reference in their entirety.

The ECG processing unit 520 may be configured to solve the inverse problem of electrocardiography to project ECG data onto a 2-dimensional or 3-dimensional heart model. A graphical display 526 may be produced from the data projected on a computer heart model to create a visual mapping of the surface potential data mapped to the heart model. ECG feature values may be represented as normalized values or percentages of a reference value of the respective feature.

Additionally or alternatively, a mapped location of scar tissue based on the ECG feature values may be presented in a graphical display 528. The ECG processing unit 520 may be configured to identify boundaries of detected scar tissue on a model heart in response to determining an overall cardiac scar burden index and torso surface locations of the electrodes identified having an affirmative scar indicator index. The display 528 presents the boundaries 530 of scar tissue along the model heart and reports the overall cardiac scar burden index. As described below, a scar burden index may be computed as a percentage of the electrodes 510 having an affirmative scar indicator index.

No imaging of the actual patient anatomy is required to produce the graphical displays 524, 526 and/or 528. Rather the ECG data is mapped to a generic, graphical computer model of a patient's torso and/or heart and a graphical display is produced without taking an actual image, such as an MRI or CT image, from the patient.

The resolution of the ECG data mapped to a graphical anatomical model will depend on the number and spacing of surface electrodes 510 used. In some examples, there may be 12 to 16 electrodes spatially distributed around the torso of patient 506. Other configurations may have more or fewer electrodes. In one embodiment, a minimum number of electrodes includes twelve electrodes arranged in two rows extending along the posterior torso and twelve electrodes arranged in two rows extending along the anterior torso for a total of twenty-four electrodes, which may be equally distributed circumferentially around the torso.

Figure 6:
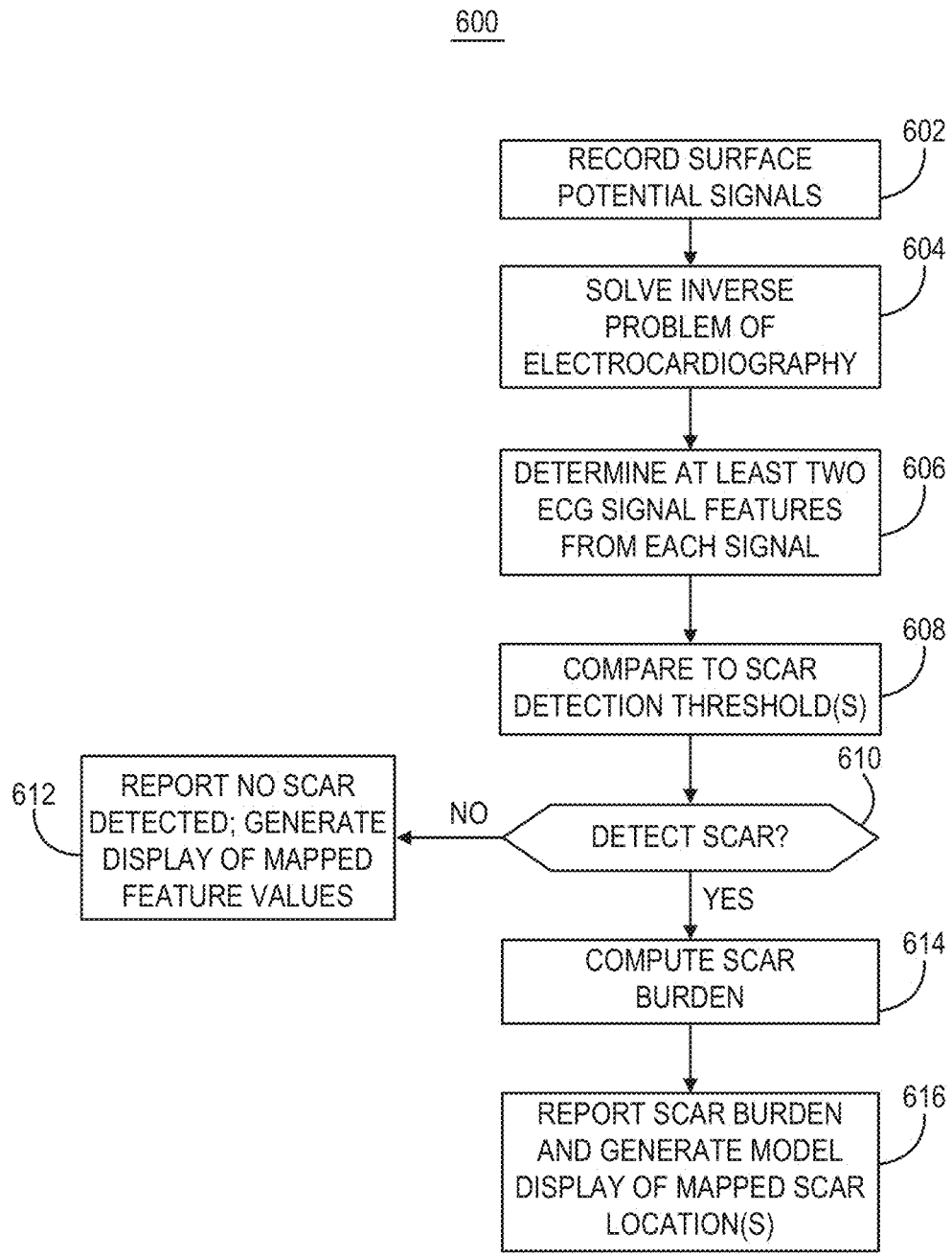
FIG. 6 is a flow chart of a method for determining a scar burden index according to one embodiment.

FIG. 6 is a flow chart 600 of a method for determining a scar burden index according to one embodiment. At block 602, surface potential signals are recorded from skin electrodes distributed on a torso of a patient, for example as shown in FIG. 5. An ECG processing unit receives the potential signals from each surface electrode via the necessary electrical conductors or in some systems potential signals may be transmitted wirelessly from a body worn device to an ECG processing unit.

A processor included in the ECG processing unit solves the inverse problem of electrocardiography using a computer model of a heart anatomy and the received potential signals at block 604. The potential signals resulting from the inverse problem solution are used to characterize heart activity on the surface of the heart model. Features are extracted from the potential signals corresponding to each of the torso-surface electrodes at block 606. In one embodiment, at least two features are determined from each signal, which may include a metric of the QRS signal amplitude, a metric of Q-wave negativity and/or a metric of QRS signal fractionation, or any combination thereof, as described previously. The potential signals and/or the determined features can be stored in a non-transitory storage medium, e.g. digital memory associated with the ECG processing unit.

A scar indicator index is determined by the processor from the potential signal features, which may be normalized or non-normalized and combined in a single index or used individually as scar indicator indices. Feature values may be normalized by determining a maximum, minimum, mean, median, mode or other reference value from all of the feature values determined from the distributed electrodes. The scar indicator indices determined for each electrode, from the potential signal produced at each surface electrode, are compared to a scar detection threshold at block 608 to identify which, if any, electrodes result in an affirmative scar indicator index. In this way, myocardial scar tissue is detected as being present at a cardiac location that corresponds to the torso-surface electrode that produced a potential signal resulting in a scar indicator index meeting a detection threshold requirement.

If scar tissue is detected at block 610 based upon one or more electrodes having an affirmative scar indicator index, a scar burden index is computed at block 614. In one embodiment, the scar burden index is computed as a proportion of the torso-surface electrodes having an affirmative scar indicator index. Additionally or alternatively, a scar burden index may be determined as an estimated myocardial surface area based on the number and location of electrodes having an affirmative scar indicator index.

The scar burden index is reported at block 616. The scar burden index may be reported with a graphical display of data derived from the surface potential signals mapped to an anatomical heart model. Data obtained from the surface potential signals can be mapped to a heart using a computer model of a heart and the potential signals. For example, this process may involve solving inverse problem of electrocardiography based on a model heart and a model torso onto which the measured surface signals are mapped. The solution of inverse problem would provide reconstructed unipolar EGM signals at points or sites on the surface of the model heart. The reconstructed unipolar EGM features may be extracted and criteria for scar detection may be applied as described above. Feature values or an indication of the presence of scar tissue can be mapped and displayed to a clinician. The boundaries of detected scar tissue may be estimated and presented on the display of a heart model based upon sites associated with affirmative scar indicator indices. If no scar is detected at block 610, this result may be reported, and a display of a heart model mapped with signal feature values or scar indicator indices may optionally be generated at block 612.

The scar burden index and estimated scar boundaries may be used by a clinician in making treatment decisions. For example, a patient being evaluated for CRT may be contraindicated for therapy if the scar burden exceeds a threshold value. Patients with a relatively high scar burden may not respond to CRT. Therefore, the scar burden index may be used as a predictor of patients that are expected to receive therapeutic benefit from CRT and those that are not. The reported scar burden at block 616 may include a recommendation for CRT therapy based on the determined scar burden exceeding a threshold scar burden (CRT not recommended) or not exceeding a threshold scar burden (CRT recommended).

Figure 7:
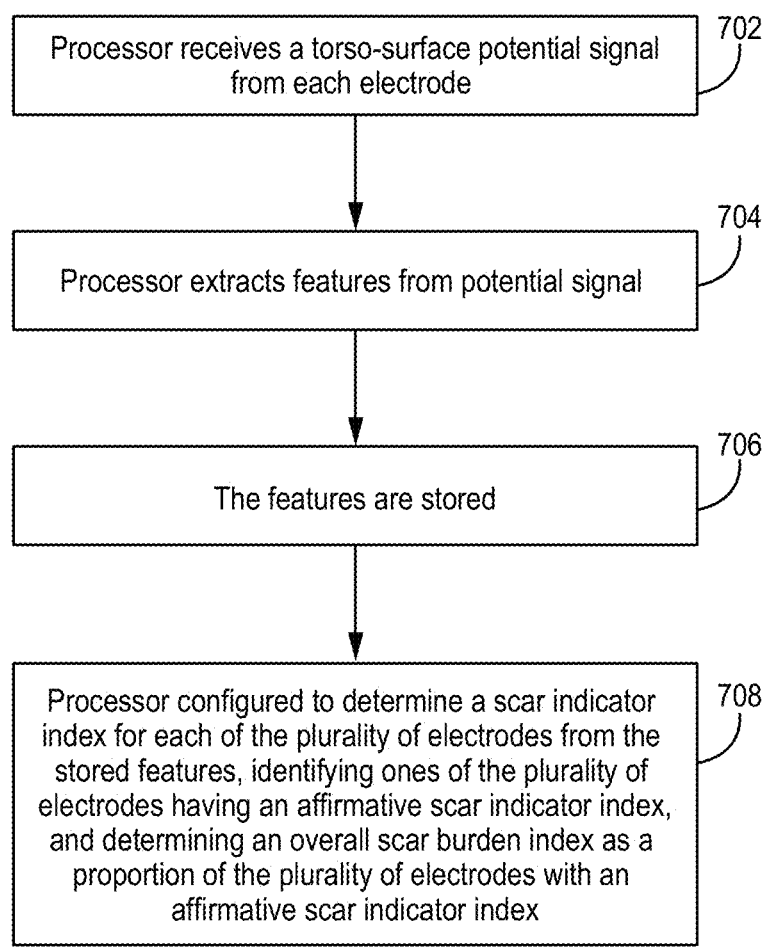
FIG. 7 is a flow chart of a method for determining a scar burden index according to one embodiment.

FIG. 7 is a flow chart of a system and/or method is disclosed for determining a scar burden index. A system and/or a method is disclosed that comprises a processor receiving means for receiving a torso-surface potential signal from each of a plurality of electrodes distributed on a torso of a patient at block 702. At block 704, a processor means extracts features of the potential signal from each of the plurality of electrodes. At block 706, the features are stored. At block 708, a processor means is configured to determine a scar indicator index for each of the plurality of electrodes from the stored features, identifying ones of the plurality of electrodes having an affirmative scar indicator index, and determining an overall scar burden index as a proportion of the plurality of electrodes with an affirmative scar indicator index.

Thus, various embodiments of a system and method for determining the presence of myocardial scar have been described. However, one of ordinary skill in the art will appreciate that various modifications may be made to the described embodiments without departing from the scope of the claims. For example, although specific examples of scar indicator indices or ECG signal features have been described, it is recognized that other indicators may be conceived and substituted in the scar detection techniques presented herein. Both an implantable system and an external system useful for determining presence of myocardial scar have been described separately, however, the techniques disclosed herein may be combined in any manner to include scar detection using one or both internal and external electrodes at the same or different time points in managing a patient and determining a patient's scar burden. These and other examples are within the scope of the following claims.

The invention claimed is:

1. A system comprising:
a processor receiving means for receiving a torso-surface potential signal from each of a plurality of electrodes distributed on a torso of a patient;
a processor means for extracting features of the potential signal from each of the plurality of electrodes;
a storing means for storing the features;
a processor means for determining a scar indicator index for each of the plurality of electrodes from the stored features, identifying ones of the plurality of electrodes having an affirmative scar indicator index, and determining an overall scar burden index as a proportion of the plurality of electrodes with an affirmative scar indicator index.

2. The system of claim 1, further comprising a processor generating means for generating a map containing anatomic locations of electrodes with an affirmative scar indicator index.

3. The system of claim 2, further comprising a display means for displaying values of the features mapped to a computer model of a patient's anatomy.

4. The system of claim 1, further comprising a processor means for determining an inverse problem of electrocardiography based on the torso-surface potential signals and an anatomical computer model of a human heart and torso.

5. The system of claim 1, further comprising a processor means for computing potentials on a surface of a computer model of a heart anatomy based on the torso-surface potential signals.

6. The system of claim 1, further comprising a processor means for identifying boundaries of scar tissue on a computer model heart in response to determining the overall cardiac scar burden index and torso surface locations of the ones of the plurality of electrodes identified with an affirmative scar indicator index.

7. The system of claim 6, further comprising a display means for displaying the boundaries of scar tissue along the model heart and the overall cardiac scar burden index.

8. The system of claim 1, wherein the features extracted from the potential signals for each of the plurality of electrodes comprise at least two of a QRS amplitude metric, a Q-wave negativity metric, and a QRS fractionation metric.

9. The system of claim 1, further comprising a processor means for estimating a scar burden surface area in response to the determined overall cardiac scar burden index and the ones of the plurality of electrodes identified with an affirmative scar indicator index.

10. The system of claim 1, further comprising reporting means for reporting the scar burden index and a therapy recommendation in response to the scar burden index.

11. A method comprising:
receiving by a processor a torso-surface potential signal from each of a plurality of electrodes distributed on a torso of a patient;
extracting by the processor features of the potential signal from each of the plurality of electrodes;
storing values of the features in a non-transitory storage medium;
determining by the processor a scar indicator index for each of the plurality of electrodes from the stored features;
identifying ones of the plurality of electrodes having an affirmative scar indicator index; and
determining an overall scar burden index as a proportion of the plurality of electrodes with an affirmative scar indicator index.

12. The method of claim 11, further comprising generating a map containing anatomic locations of electrodes with an affirmative scar indicator index.

13. The method of claim 12, further comprising displaying values of the features mapped to a computer model of a patient's anatomy.

14. The method of claim 11, further comprising determining an inverse problem of electrocardiography based on the torso-surface potential signals and an anatomical computer model of a human heart and torso.

15. The method of claim 11, further comprising computing potentials on a surface of a computer model of a heart anatomy based on the torso-surface potential signals.

16. The method of claim 11, further comprising identifying boundaries of scar tissue on a computer model of a heart in response to determining the overall cardiac scar burden index and torso surface locations of the ones of the plurality of electrodes identified with an affirmative scar indicator index.

17. The method of claim 16, further comprising displaying the boundaries of scar tissue along the computer model of the heart and the overall cardiac scar burden index.

18. The method of claim 11, wherein extracting the features from the potential signals for each of the plurality of electrodes comprises determining at least two of a QRS amplitude metric, a Q-wave negativity metric, and a QRS fractionation metric.

19. The method of claim 11, further comprising estimating a scar burden surface area in response to the determined overall cardiac scar burden index and the ones of the plurality of electrodes identified with an affirmative scar indicator index.

20. The method of claim 11, further comprising reporting the scar burden index and a therapy recommendation in response to the scar burden index.

21. A non-transitory, computer readable storage medium comprising instructions for causing a processor of a medical device system to perform a method, the method comprising:
receiving a torso-surface potential signal from each of a plurality of electrodes distributed on a torso of a patient;
extracting features of the potential signal from each of the plurality of electrodes;
storing values of the features in a non-transitory storage medium;
determining a scar indicator index for each of the plurality of electrodes from the stored features;
identifying ones of the plurality of electrodes having an affirmative scar indicator index; and
determining an overall scar burden index as a proportion of the plurality of electrodes with an affirmative scar indicator index.

22. An apparatus for determining presence of myocardial scar tissue, comprising:
sensing means for receiving a torso-surface potential signal from each of a plurality of electrodes distributed on a torso of a patient;
processing means for extracting features of the potential signal from each of the plurality of electrodes;
storing means for storing values of the features in a non-transitory storage medium;
processing means for determining a scar indicator index for each of the plurality of electrodes from the stored features;
processing means for identifying ones of the plurality of electrodes having an affirmative scar indicator index; and
processing means for determining an overall scar burden index as a proportion of the plurality of electrodes with an affirmative scar indicator index.

* * * * *